(12) United States Patent
Duan et al.

(10) Patent No.: US 11,125,733 B2
(45) Date of Patent: Sep. 21, 2021

(54) DIGESTIVE TRACT MEDICATION ADMINISTRATION SYSTEM AND MEDICATION ADMINISTRATION CAPSULE

(71) Applicant: Ankon Medical Technologies (Shanghai) Co., LTD., Shanghai (CN)

(72) Inventors: Xiaodong Duan, Pleasanton, CA (US); Shaobang Zhang, Shanghai (CN)

(73) Assignee: ANKON MEDICAL TECHNOLOGIES (SHANGHAI) CO., LTD., Shanghai (CN)

( * ) Notice: Subject to any disclaimer, the term of this patent is extended or adjusted under 35 U.S.C. 154(b) by 512 days.

(21) Appl. No.: 16/248,806

(22) Filed: Jan. 16, 2019

(65) Prior Publication Data

US 2019/0219553 A1   Jul. 18, 2019

(30) Foreign Application Priority Data

Jan. 16, 2018 (CN) .......................... 20180039175.1

(51) Int. Cl.
  *G01N 33/00* (2006.01)
  *A61B 5/07* (2006.01)
  *A61B 1/04* (2006.01)
  *A61B 5/05* (2021.01)
  *A61M 31/00* (2006.01)
  *A61J 3/07* (2006.01)
  *A61B 5/00* (2006.01)

(52) U.S. Cl.
  CPC ......... *G01N 33/0055* (2013.01); *A61B 1/041* (2013.01); *A61B 5/05* (2013.01); *A61B 5/07* (2013.01); *A61B 5/073* (2013.01); *A61B 5/4839* (2013.01); *A61J 3/07* (2013.01); *A61M 31/002* (2013.01)

(58) Field of Classification Search
  None
  See application file for complete search history.

(56) References Cited

U.S. PATENT DOCUMENTS

2013/0303847 A1\*  11/2013  Sitti .................. A61B 1/00158
                                                              600/104

\* cited by examiner

*Primary Examiner* — Robert A Wax
*Assistant Examiner* — Randeep Singh
(74) *Attorney, Agent, or Firm* — Treasure IP Group, LLC (57) ABSTRACT

A digestive tract medication administration system and a medication administration capsule are provided. In an assembled state, with the constraint of a limit structure formed by a rotation limit pin on an inner shell of the capsule and a rotation limit slot in an outer shell of the capsule, and an angle exists between the N-S directions of the first magnetic column and the second magnetic column, a torque is present between the two magnetic columns, which makes parts inside the capsule tightly coupled. When an external magnetic field is applied, at least one or both of the two magnetic columns rotate under the action of the external magnetic field. When the external magnetic field is applied, the administration ports are in opened state, and when the external magnetic field is removed, the administration ports are in closed state.

17 Claims, 7 Drawing Sheets

DIGESTIVE TRACT MEDICATION ADMINISTRATION SYSTEM AND MEDICATION ADMINISTRATION CAPSULE

CROSS REFERENCE TO RELATED APPLICATIONS

This application claims priority to Chinese Patent Application No. 201810039175.1 filed on Jan. 16, 2018, the contents of which are incorporated by reference herein.

TECHNICAL FIELD

The invention relates to the technical field of a medical apparatus/system, especially refers to a swallowable digestive tract medication administration system, and specifically refers to a magnetically controlled digestive tract medication administration system and a medication administration capsule.

BACKGROUND OF THE INVENTION

Because of the accelerated pace of work and uneven diet, modern people are exposed to an increasing incidence of digestive tract diseases which have become common in affecting the health of modern people. However, with a total length of over 9 meters, the human digestive tract in the shape of long and thin tube is distributed between various organs of the human body and shows an irregular and sealed structure which poses huge challenges to targeted administration and treatment for upper gastrointestinal diseases.

In view of the particularity of digestive tract, capsule miniaturization is a goal of the industry. To realize targeted administration of medications, in existing digestive tract capsules, the medication administration capsules generally incorporate a drive mechanism as a core component to control the position where the medication is administered. To a great extent, the degree of miniaturization of the capsule is determined by drive modes of the drive mechanism. The existing drive modes mainly include: motor drive, electromagnetic drive, compression spring drive, etc., or opening the capsule hole by these modes. Since the drive mechanism is integrated in the medication administration capsule, and the size of the capsule suitable for human swallowing is limited, the larger volume the drive mechanism occupies in the capsule, the less capacity is left for loading of medications. So, in view of the miniature size of the capsule, integration of a drive mechanism will make the capsule structure complicated, with low reliability and small capacity.

Therefore, it is necessary to propose a magnetically controlled digestive tract medication administration system and a split-type medication administration capsule, to simplify the capsule structure, increase the capsule capacity under a certain capsule size limit and realize targeted medication administration and treatment.

SUMMARY OF THE INVENTION

The present invention discloses a medication administration capsule, comprising an inner shell, an outer shell, a first magnetic cylinder, a second magnetic cylinder and medicinal powders, wherein the outer shell is larger than the inner shell, and the outer shell and the inner shell are matched with each other and are rotationally sealed; wherein the first magnetic cylinder is fixed in the inner shell, and the outer diameter of the first magnetic cylinder is matched with the inner diameter of the inner shell; wherein the second magnetic cylinder is fixed in the outer shell, and the outer diameter of the second magnetic cylinder is matched with the inner diameter of the outer shell; wherein the first magnetic cylinder and the second magnetic cylinder are radially polarized, and the first magnetic cylinder and the second magnetic cylinder are set to present an angle of >0° and <90° between the N-S directions of two poles of the two magnetic cylinders; wherein the medicinal powder is put between the first magnetic cylinder and the second magnetic cylinder.

In one embodiment of the present invention, at least one administering window is cut in the outer shell, having the same quantity as the administering window cut in the inner shell, and the administering windows in the outer shell and the inner shell are matched in pairs; when no external magnetic field is applied, the administering windows are misaligned and covered up by the outer shell and the inner shell; and when an external magnetic field is applied, the administering windows overlap as the outer shell and the inner shell of the capsule rotate relatively under the action of magnetic field, and the administering windows are opened.

In another embodiment of the present invention, two administering windows are cut in the annular wall of the outer shell and two administering windows are cut in the annular wall of the inner shell; the four administering windows matched in pairs are misaligned and covered up by the outer shell and the inner shell when an external magnetic field is not applied, and are opened by relative rotation between the outer shell and the inner shell when the external magnetic field is applied.

In other embodiment of the present invention, three or more than three administering windows are cut in the annular wall of the inner shell, having the same quantity as the administering windows of the inner shell cut in the annular wall of the outer shell, and the administering windows in the outer shell and the inner shell are matched in pairs; when an external magnetic field is not applied, the administering windows are misaligned and covered up by the outer shell and the inner shell; and when the external magnetic field is applied, the administering windows are opened as the outer shell and the inner shell rotate relatively under the action of magnetic field.

The present invention further discloses a digestive tract medication administration system, comprising an external magnet and a medication administration capsule, wherein the external magnet locates outside human body, and the medication administration capsule enters the digestive tract of the human body when used; and the medication administration capsule is described as set above.

DETAILED DESCRIPTION OF THE PREFERRED EMBODIMENTS

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Figure 1:
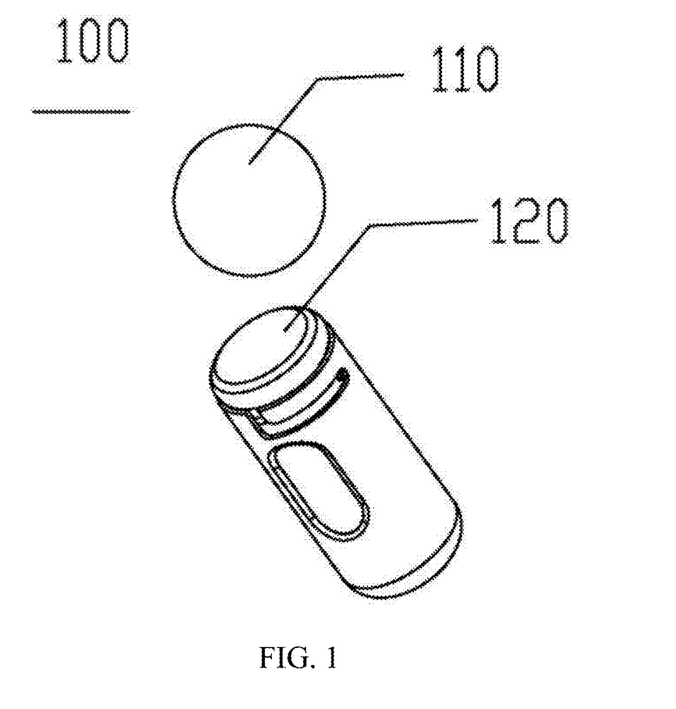
FIG. 1 shows a schematic illustration of a digestive tract medication administration system in accordance with the present invention.

Referring to FIG. 1, a digestive tract medication administration system 100 comprises an external magnet 110 and a medication administration capsule 120, wherein the medication administration capsule 120 is microstructured and enters human digestive tract through the mouth, and the external magnet 110 is located outside the human body.

The matching of the outer shell and the inner shell means that the outer shell has the same shape as the inner shell, can cooperate with each other and can be tightly coupled. In one embodiment, the outer shell and the inner shell are both in a hollow cylindrical shape, and the inner diameter of the outer shell is larger than the outer diameter of the inner shell a size from 0 to 0.02 mm.

The matching of the first magnetic cylinder and the inner shell means that the first magnetic cylinder and the inner shell are tight fit to an integration. In one embodiment, the first magnetic cylinder and the inner shell are fixed with glue to an integration.

The matching of the second magnetic cylinder and the outer shell means that the second magnetic cylinder and the outer shell are tight fit to an integration. In one embodiment, the second magnetic cylinder and the outer shell are fixed with glue to an integration.

Further rotationally sealed means that a seal is provided through rotation.

Figure 2:
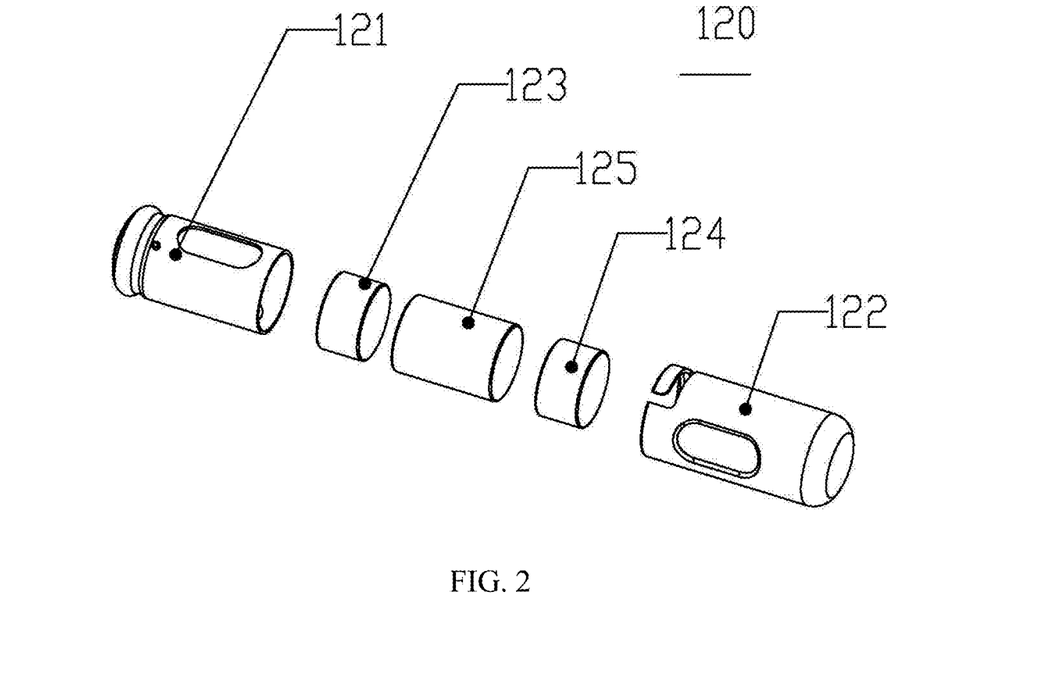
FIG. 2 shows an exploded view of a medication administration capsule shown in FIG. 1.

FIG. 2 shows the exploded view of the medication administration capsule 120. As shown in the figure, the medication administration capsule 120 comprises an inner shell 121, an outer shell 122, a first magnetic cylinder 123, a second magnetic cylinder 124 and medicinal powder 125, wherein the outer shell 122 is larger than the inner shell 121 in size. The inner shell 121 and the outer shell 122 are matched with each other and are latched by rotation to form the entire medication administration capsule 120. The first magnetic cylinder 123 is fixed in the inner shell 121, and the outer diameter of the column is matched with the inner diameter of the inner shell 121. The second magnetic cylinder 124 is fixed in the outer shell 122, and the outer diameter of the second column 124 is matched with the inner diameter of the outer shell 122. The first magnetic cylinder 123 and the second magnetic cylinder 124 are radially polarized. The medicinal powder 125 is fed between the first magnetic cylinder 123 and the second magnetic cylinder 124, without a requirement for the shape of the medicinal powder 125. In one embodiment, the first magnetic cylinder 123 is first installed into the inner shell 121, then the medicinal powder 125 filled in the space above the first magnetic cylinder 123 in the inner shell 121, and finally the outer shell 122 installed with the second magnetic cylinder 124 and the inner shell 121 are assembled to form the medication administration capsule 120. In another embodiment, the medicinal powder 125 is compressed into a cylindrical shape matching the shape of the first magnetic cylinder 123 and the second magnetic cylinder 124, and then assembled into the medication administration capsule 120 with other components.

Figure 3:
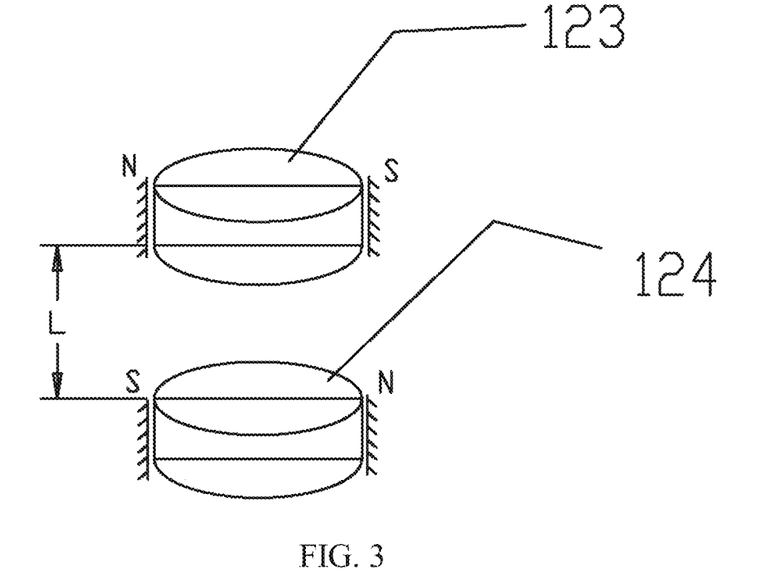
FIG. 3 shows a schematic illustration of two magnetic cylinders inside the medication administration capsule in a natural state without external force.

FIG. 3 shows a schematic illustration of two magnetic cylinders inside the medication administration capsule in a natural state without external force. As shown in the figure, in a natural state without any external force, the first magnetic cylinder 123 and the second magnetic cylinder 124 are separated by a certain distance L, which is the thickness of the medicinal powder 125 sandwiched in the middle. In addition, the first magnetic cylinder 123 and the second magnetic cylinder 124 are radially polarized, and radial polarization means that the lines connecting N and S poles of the magnetic cylinders are aligned with the diameters. In one embodiment of the present invention, as shown in FIG. 3, in a natural state without any external force (including the external magnetic field or mechanical limit structure as described below), the first magnetic cylinder 123 and the second magnetic cylinder 124 have opposite N-S directions, while the two magnetic cylinders are parallel and coaxial, subject to radial constraint, and can rotate freely. When there are no external magnetic field and mechanical limit structure applied for rotation limit, in the case of constant end of the two magnetic cylinders face spacing, a certain distance is kept between the two magnetic cylinders (the distance is the thickness of the medicinal powder 125), the N-S directions of the two magnetic cylinders are opposite, and the two magnetic cylinders are attracted by magnetic force. In an example, as shown in FIG. 3, the N pole of the first magnetic cylinder 123 is on the left side, and the S pole is on the right side; the N pole of the second magnetic cylinder 124 is on the right side, and the S pole is on the left side. Note that the N-S directions of the two magnetic cylinders in this case are opposite as shown in FIG. 3, that is, when no external force is applied, on the same side, the pole of one magnetic cylinder is N and the pole of the other is S, and vice versa.

In accordance with the present invention, the radial polarization of the first magnetic cylinder 123 and the second magnetic cylinder 124 is achieved by: first forming a desired shape of column with magnetic powder, then sintering, and finally magnetizing along the radial direction with an electromagnetic field. Generally, when a magnet is manufactured, the N and S poles of the magnet are determined according to the magnetic field applied.

Figure 4:
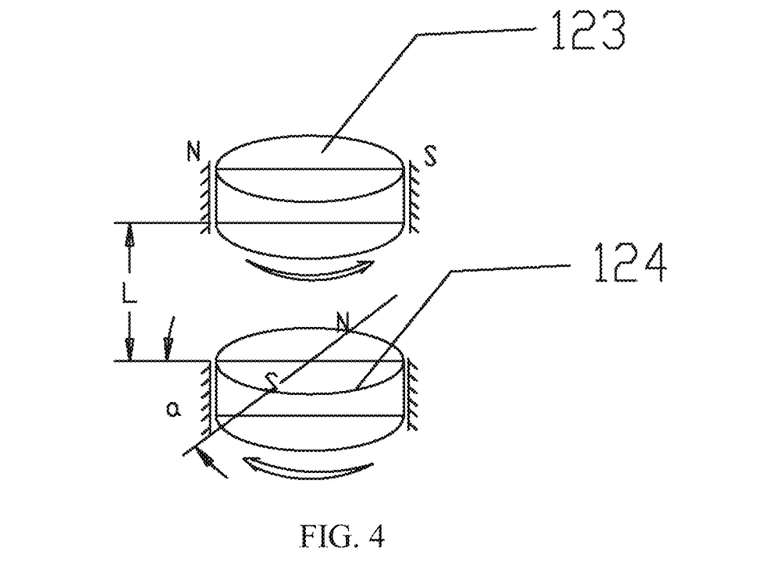
FIG. 4 shows a schematic illustration of two magnetic cylinders inside the medication administration capsule in a state, wherein an angle exists between the lines connecting two poles of the two magnetic cylinders.

FIG. 4 shows a schematic illustration of two magnetic cylinders inside the medication administration capsule in a state, wherein an angle (a) exists between the lines connecting two poles of the two magnetic cylinders. Note that, with no external magnetic field, the angle is formed depending on the action of the limit structure as described below; when an external magnetic field is applied, both the external magnetic field and the limit structure can lead to this state. Moreover, in the state of use after assembly, an angle always exists between the lines connecting the N and S poles of the two magnetic cylinders. The angle $\alpha$ may be any one, provided that the two magnetic cylinders can rotate. In one embodiment of the present invention, the angle meets $0°<\alpha<90°$. In this case, at least one of the magnetic cylinders rotates relative to the other one, or both rotate relative to each other. Since there is a mutual attraction between the N pole of one magnetic cylinder and the S pole of the other one, or the S pole of one magnetic cylinder and the N pole of the other one, when the angle $\alpha$ is present, a torque can be generated between the two magnetic cylinders. Under the action of the torque, two magnetic cylinders will bind more tightly.

Figure 5:
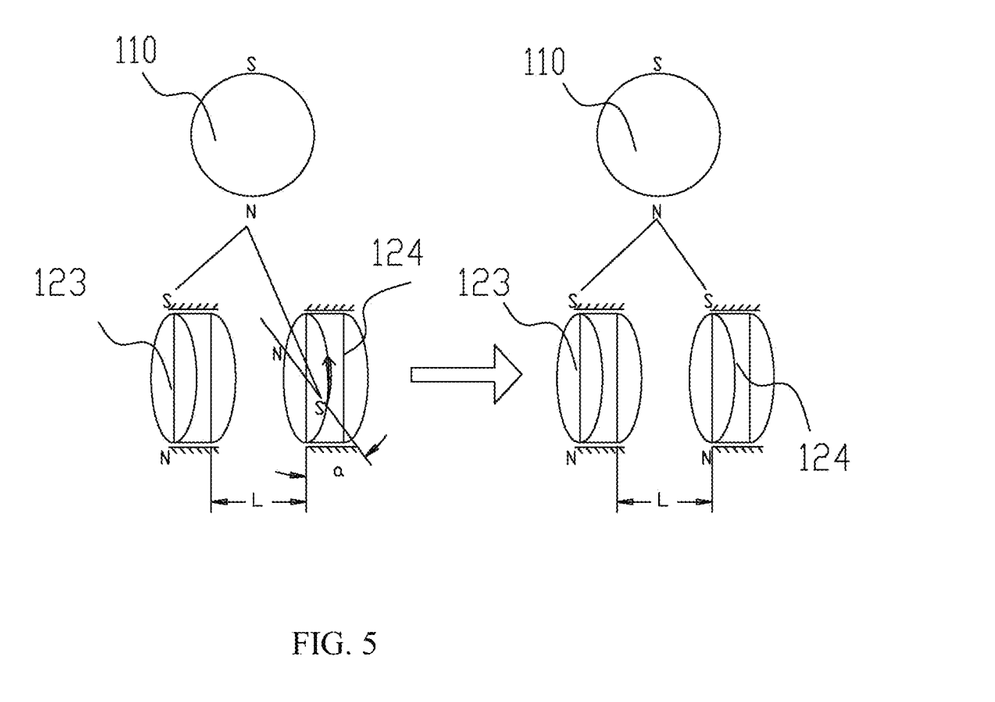
FIG. 5 shows a schematic illustration of two magnetic cylinders rotating when an external magnetic field is applied.

When an external magnetic field is applied, in an extreme case, the action of the external magnetic field makes the two magnetic cylinders same in N-S directions. That is, the external magnetic field enables N poles or S poles of the two magnetic cylinders to be at the same sides. In this case, the torque between the two magnetic cylinders is the biggest. In one embodiment of the present invention, as shown in FIG. 5, the first magnetic cylinder 123 and the second magnetic cylinder 124 are placed horizontally, and the left image shows a state when an external magnetic field is initially applied, wherein the initial angle $\alpha$ between the N-S directions of the first magnetic cylinder 123 and the second magnetic cylinder 124 is shown. The angle is limited by the limit structure described below. When the N pole of the external magnetic field approaches the first magnetic cylinder 123 and the second magnetic cylinder 124, the two magnetic cylinders can not move vertically away from or close to the external magnetic field as they are housed in the medication administration capsule 120, but at least one of the magnetic cylinders rotates instead. When the N pole of the external magnetic field gradually approaches the first magnetic cylinder 123 and the second magnetic cylinder 124, the S pole of the first magnetic cylinder 123 can be attracted while the N pole of the second magnetic cylinder can be repelled. At this point, the second magnetic cylinder 124 can automatically rotate as it cannot move away from the external magnetic field in the vertical direction, so that the N pole of the magnetic cylinder moves away from the N pole of the external magnetic field, and the S pole of the magnetic cylinder approaches the N pole of the external magnetic field. Thus, the attraction of the external magnetic field to the first magnetic cylinder 123 and the second magnetic cylinder 124 gradually increases, so does the angle $\alpha$ between the two magnetic cylinders. As a result, the torque generated is also increased. In this case, the outer shell 122 is driven by the second magnetic cylinder 124 and the inner shell 121 is driven by the first magnetic cylinder 123. At least one or both of the two magnetic cylinders will rotate relative to the other one and the angle of rotation is consistent with the angle $\alpha$. When the external magnetic field continues to infinitely approach the first magnetic cylinder 123 and the second magnetic cylinder 124, the N pole of the second magnetic cylinder 124 is deflected to the opposite side, and the first magnetic cylinder 123 and the second magnetic cylinder 124 are in the same direction, which the rotation torque generated between the two is the largest.

As the person having ordinary skill in the art can comprehend, in another embodiment of the present invention, when the S pole of the external magnetic field approaches the first magnetic cylinder 123 and the second magnetic cylinder 124, the S pole of the first magnetic cylinder 123 can repel it, making the first magnetic cylinder 123 rotate relative to the second magnetic cylinder 124. Since the first magnetic cylinder 123 is fixed in the inner shell 121, the rotation of the first magnetic cylinder 123 can drive the inner shell 121 to rotate relative to the outer shell 122. As the external magnetic field may approach from different directions, it is possible to make one or both of the two magnetic cylinders rotate. For example, in one embodiment of the present invention, when the external magnetic field approaches, at least one of the first magnetic cylinder 123 and the second magnetic cylinder 124 rotates relative to the other because of the repulsion of equal poles; in another embodiment of the present invention, when the external magnetic field approaches, both of the first magnetic cylinder 123 and the second magnetic cylinder 124 rotate. In either case, the result is that the first magnetic cylinder 123 and the second magnetic cylinder 124 rotates relative to each other, driving the inner shell 121 and the outer shell 122 to rotate relative to each other.

Figure 6:
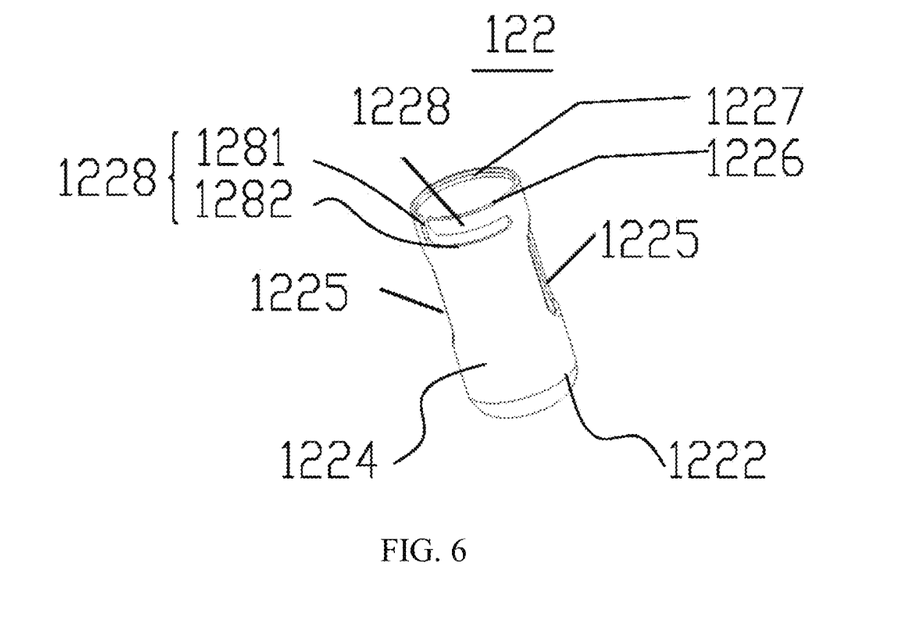
FIG. 6 shows a structural view of an outer shell of the medication administration capsule.

FIG. 6 shows a structural view of the outer shell 122. The outer shell 122 has a cup-shaped structure, comprising a cup bottom 1222, an annular wall 1224 extending from and perpendicular to the cup bottom 1222, and a circular opening 1226 opposite to the cup bottom 1222. Close to the circular opening 1226, a rotation limit slot 1228 is cut in the annular wall 1224, which cooperates with a rotation limiting pin to be described below to provide a movement track for the rotation limiting pin. The rotation limit slot 1228 comprises an entrance part 1281 at a certain angle to the plane of the circular opening 1226 and a movement part 1282 parallel to the plane of the circular opening 1226, and the entrance part 1281 is in connection with the movement part 1282 to form a L-shaped slot. In one embodiment of the present invention, the entrance part 1281 is perpendicular to the movement part 1282. In another embodiment of the present invention, the entrance part 1281 is at an obtuse angle to the movement part 1282. In still another embodiment of the present invention, the entrance part 1281 is at an acute angle to the movement part 1282. Preferably, the junction between the entrance part 1281 and the movement 1282 is a smooth curved surface.

Figure 7:
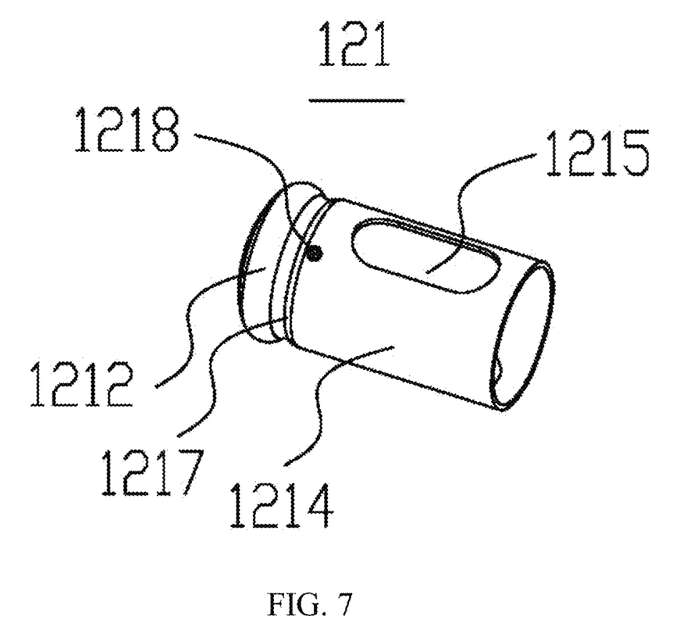
FIG. 7 shows a structural view of an inner shell of the medication administration capsule.

FIG. 7 shows a structural view of the inner shell 121. The inner shell 121 has a cap-shaped structure, comprising a cap top 1212 and an annular wall 1214 perpendicular to the cap top 1212. A rotation limiting pin 1218 is designed near the junction of the cap top 1212 and the annular wall 1214. The rotation limiting pin 1218 cooperates with the rotation limit slot 1228 for rotationally engaging the inner shell 121 with the outer shell 122.

Before assembly, the N-S directions of the first magnetic cylinder 123 and the second magnetic cylinder 124 need to be measured by an instrument, and according to the directions measured, the first magnetic cylinder 123 is mounted in the inner shell 121, and the second magnetic cylinder 124 in the outer shell 122. To determine the mounting angles, the positions of the rotation limit slot 1228 and the rotation limiting pin 1218 need to be considered. In the state of normal use where the external magnetic field is not applied, the rotation limit slot 1228 and the rotation limiting pin 1218 form a limit structure which constrains the positions of the first magnetic cylinder 123 and the second magnetic cylinder 124, so that the angle $\alpha$ ($0°<\alpha<90°$) exists between the N-S directions of the two magnetic cylinders. Presence of the angle α ensures an ever-present torque between the first magnetic cylinder 123 and the second magnetic cylinder 124 is always present, so that the entire structure is always in a tightened state. At the same time, there is always an attraction between the first magnetic cylinder 123 and the second magnetic cylinder 124. In this way, the magnetic cylinders can be unlikely to fall out of the medication administration capsule 120 in the digestive tract during use, thus meeting safety requirements.

To further enhance safety, in one embodiment of the present invention, internal threads 1227 are cut at the circular opening 1226 of the outer shell 122, and external threads 1217 are cut at the junction of the cap top 1212 and the annular wall 1214 of the inner shell 121, and the external threads 1217 and the internal threads 1227 are on a threaded connection. The external threads 1217 fit the internal threads 1227. As thus, even in a special case where the rotation limiting pin 1218 on the inner shell 121 is rotated to the entrance part 1281, but there is still a risk of falling off on account of gastrointestinal peristalsis or external force, safety in use of the medication administration capsule 120 can be ensured depending on the threaded connection between the external threads 1217 and the internal threads 1227.

Referring to FIG. 6 and FIG. 7, in one embodiment of the present invention, an administering window 1225 is cut in the annular wall 1224 of the outer shell 122, in the vicinity of the entrance part 1281 of the rotation limit slot 1228, and an administering window 1215 is cut in the annular wall 1214 of the inner shell 121, in the vicinity of the rotation limiting pin 1218. The two administering windows 1225 and 1215 are paired with each other. When the targeted lesion is not reached, an external magnetic field is not required, and the two ports are misaligned and covered up by the shells at that point to reduce waste of the medication powder 125. When the medication administration capsule 120 reaches the targeted lesion, an external magnetic field is applied, and under the action of magnetic force, the outer shell 122 and the inner shell 121 rotate relatively to make the two administering windows aligned till fully opened. At this point, the medicinal powder 125 in the capsule 120 is released, and the digestive juice comes into contact with the medication powder 125 to accelerate its release.

In the case wherein each of the inner shell 121 and the outer shell 122 is designed with one administering window, the directions of planes formed by the two administering windows and the central axis of the medication administration capsule 120 are perpendicular to each other, and the two ports are adjacent to each other. When there is no external magnetic field, the two administering windows are covered mutually, making the medication administration capsule 120 closed. When an external magnetic field is applied, the two administering windows reach an alignment by rotation of the inner shell 121 and the outer shell 122, making the medication administration capsule 120 opened for administration of medications.

In another embodiment of the present invention, two administering windows 1225 are cut in the annular wall 1224 of the outer shell 122 at two sides of the rotation limit slot 1228. Preferably, the two administering windows 1225 are on the same axial face of the annular wall 1224 of the outer shell 122. Two administering windows 1215 are cut in the annular wall 1214 of the inner shell 121, and preferably, one of the administering windows 1215 is close to the rotation limiting pin 1218 and the two administering windows 1215 are symmetrical about the central axis of the capsule 120; more preferably, the two administering windows 1215 are on the same axial face of the annular wall 1214 of the inner shell 121. In the embodiment, wherein each of the inner shell 121 and the outer shell 122 is designed with two administering windows, when there is no external magnetic field, the first direction where the two administering windows 1215 of the inner shell 121 are in is at an angle to the second direction where the two administering windows 1225 of the outer shell 122 are in. It is only necessary to ensure that all of the administering windows of the medication administration capsule 120 are closed when no external magnetic field is applied. When an external magnetic field is applied, under the action of magnetic field, the inner shell 121 and the outer shell 122 rotate relative to each other, turning the two administering windows 1215 of the inner shell 121 and the two administering windows 1225 of the outer shell 122 to an open state. As thus, when the targeted lesion is reached, the ports are opened to release the medicinal powder 125 out of the medication administration capsule 120. In addition, the digestive juice comes into contact with the administering windows and the medicinal powder 125 to accelerate its release. When the targeted lesion is not reached, the administering windows are closed to reduce waste of the medicinal powder 125. Therefore, the purpose of administration of medications to a targeted lesion for treatment can be achieved, so as to improve therapeutic effect and save the cost of medicinal powders.

As the person having ordinary skill in the art can comprehend, in accordance with the essence of the invention, over three administering windows 1225 can be cut in the annular wall 1224 of the outer shell 122, having the same quantity as the administering windows 1215 cut in the annular wall 1214 of the inner shell 121, and the administering windows in the outer shell 122 and the inner shell 121 are matched in pairs. When an external magnetic field is not applied, under the action of the limit structure formed by the rotation limit slot and rotation limit spin, the administering windows are misaligned and covered up by the outer shell 122 and the inner shell 121; and when an external magnetic field is applied, the administering windows are opened as the outer shell 122 and the inner shell 121 rotate relatively under the action of magnetic field.

The number of the administering windows may vary depending on the size of the administering window and the medication administration capsule 120. Theoretically, there may be one or more or at least one administering window. The administering windows 1225 cut in the outer shell 122 are the same in quantity as the administering windows 1215 cut in the inner shell 121. They are matched in pairs, allowing to be arranged at equal spacing or arranged at unequal spacing, provided that the administering windows 1225 and 1215 are misaligned and covered up when no external magnetic field is applied, the administering windows 1225 and 1215 are aligned and opened as the outer shell 122 and the inner shell 121 rotate relatively when an external magnetic field is applied. Preferably, the number of the administering windows 1225 and the administering windows 1215 are 1-10, respectively.

The positions of the rotation limit slot 1228, the rotation limiting pin 1218 and the administering windows are specially designed for achieving the purpose of medications administration. So, when no magnetic field is applied, the plane formed by the administering window 1215 near the rotation limiting pin 1218 of the inner shell 121 and the central axis of the medication administration capsule 120 is in the first direction; the plane formed by the administration 1225 near the rotation limit slot 1228 of the outer shell 122 and the central axis of the medication administration capsule 120 is in the second direction. The first direction is at an angle to the second direction.

To achieve the above technical effects, in one embodiment of the present invention, the N-S direction of the first magnetic cylinder 123 is the same as the axial direction of the administering window 1215 of the inner shell 121 during installation, that is, the N-S direction of the first magnetic cylinder 123 passes through the administering window 1215 of the inner shell 121. The N-S direction of the second magnetic cylinder 124 needs to be perpendicular to the axial direction of the administering window 1225 of the outer shell 122. In another embodiment of the present invention, during installation, the N-S direction of the first magnetic cylinder 123 is perpendicular to the axial direction of the administering window 1215 of the inner shell 121, while the N-S direction of the second magnetic cylinder 124 is parallel to the axial direction of the administering window 1225 of the outer shell 122. That is, when the external magnetic field is not applied, the N-S directions of the first magnetic cylinder 123 and the second magnetic cylinder 124 has an angle, but both are in the same axial direction. The axial direction of the two administering windows 1215 of the inner shell 121 is at an angle to the axial direction of the two administering windows 1225 of the outer shell 122; preferably, the angle is 90°. In this case, after assembly, when the external magnetic field is not applied, the administering windows 1215 and the administering windows 1225 are covered up by the outer shell 122 and the inner shell 121 as an angle exists between axial directions of the administering windows, even a 90°, thereby making the whole medication administration capsule 120 closed.

Figure 8:
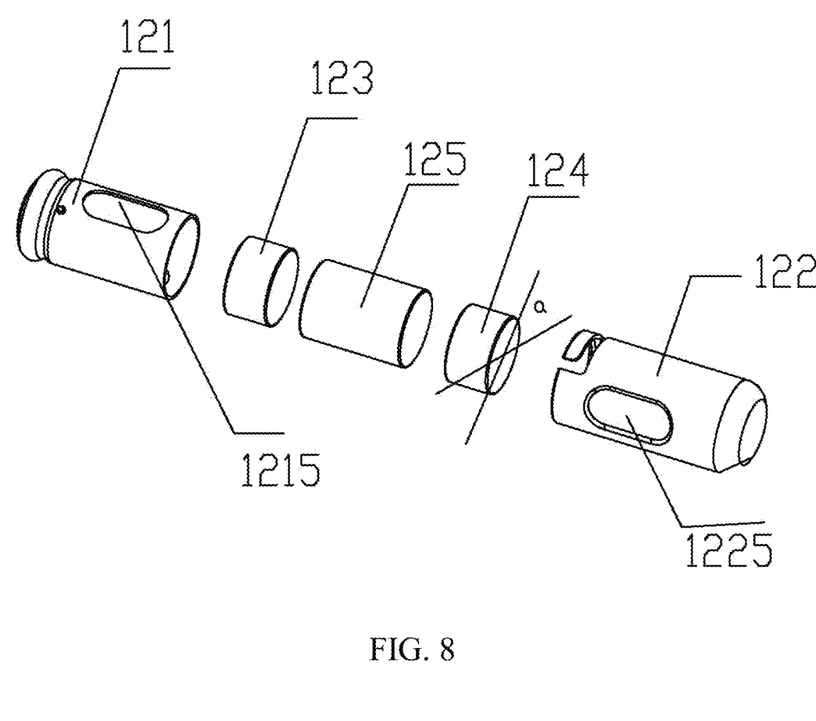
FIG. 8 shows an exploded view of the medication administration capsule when an external magnetic field is applied.

FIG. 8 shows an exploded view of the medication administration capsule 120 when an external magnetic field is applied. As shown in the figure, the first magnetic cylinder 123 is integrally mounted in the inner shell 121, the second magnetic cylinder 124 is integrally mounted in the outer shell 122, and the medicinal powder 125 is sandwiched between the first magnetic cylinder 123 and the second magnetic cylinder 124. Under the action of the rotation limit slot 1228 and the rotation limiting pin 1218, when the external magnetic field is not applied, there is always an angle between the N-S directions of the first magnetic cylinder 123 and the second magnetic cylinder 124, so that the administering windows 1215 and 1225 are covered up by the annular walls of the outer shell 122 and the inner shell 121. When an external magnetic field is applied, such as in the embodiment shown in FIG. 8, the second magnetic cylinder 124 rotates along the central axis of the medication administration capsule 120 because of the action of magnetic force, driving the outer shell 122 to rotate. As thus, the administering windows 1215 and 1225 covered up by the outer shell 122 and the inner shell 121 can come out as the inner shell 121 and outer shell 122 rotate relative to each other to make the medication administration capsule 120 open for medication administration.

In one embodiment of the present invention, the administering windows 1215 and 1225 can be in various shapes and sizes, for example, elliptical, rectangular, square, trapezoidal, star, triangular, etc., and the widths thereof are positively correlated with the angle α. The requirements of the present invention can be met, provided the shapes of the administering windows 1215, 1225 allow them to be closed and opened during rotation. In addition, in the same embodiment, the administering windows 1215 and 1225 matched in pairs are preferably the same in shape.

In one embodiment of the present invention, the external magnetic field may be either a magnetic ball or a magnetic cylinder, not limited to a column.

Figure 9:
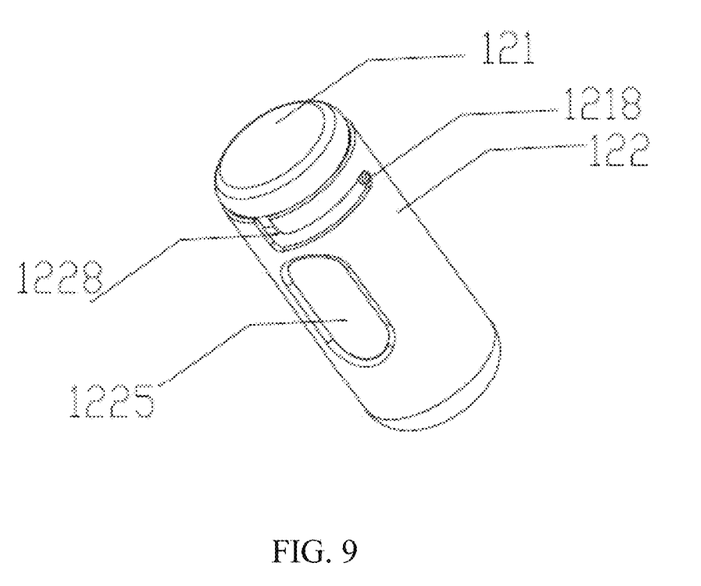
FIG. 9 shows an assembled view of the medication administration capsule.

FIG. 9 shows an assembled view of the medication administration capsule 120. After assembly, the rotation limiting pin 1218 and the rotation limit slot 1228 fitting each other form a limit structure which provides a number of functions, including: guide the relative rotation of the inner shell 121 or the outer shell 122; combine the medication administration capsule 120 firmly for not spitting in use; maintain an angle between the N-S directions of the first magnetic cylinder 123 and the second magnetic cylinder 124, which produces an always existing torque between the two magnetic cylinders and thereby enhances the mutual joining force of the inner shell 121 and the outer shell 122.

In a word, the limit structure formed by the rotation limiting pin 1218 and the rotation limit slot 1228 together is intended for guiding and limiting purposes in relative rotation of the inner shell 121 and the outer shell 122. Those skilled in the art can understand that the limit structure is not limited to the rotation limit slot, the rotation limiting pin, and may be other forms. For example, in one embodiment of the invention, the limit structure is a combination of bump and slide rail.

Figure 10:
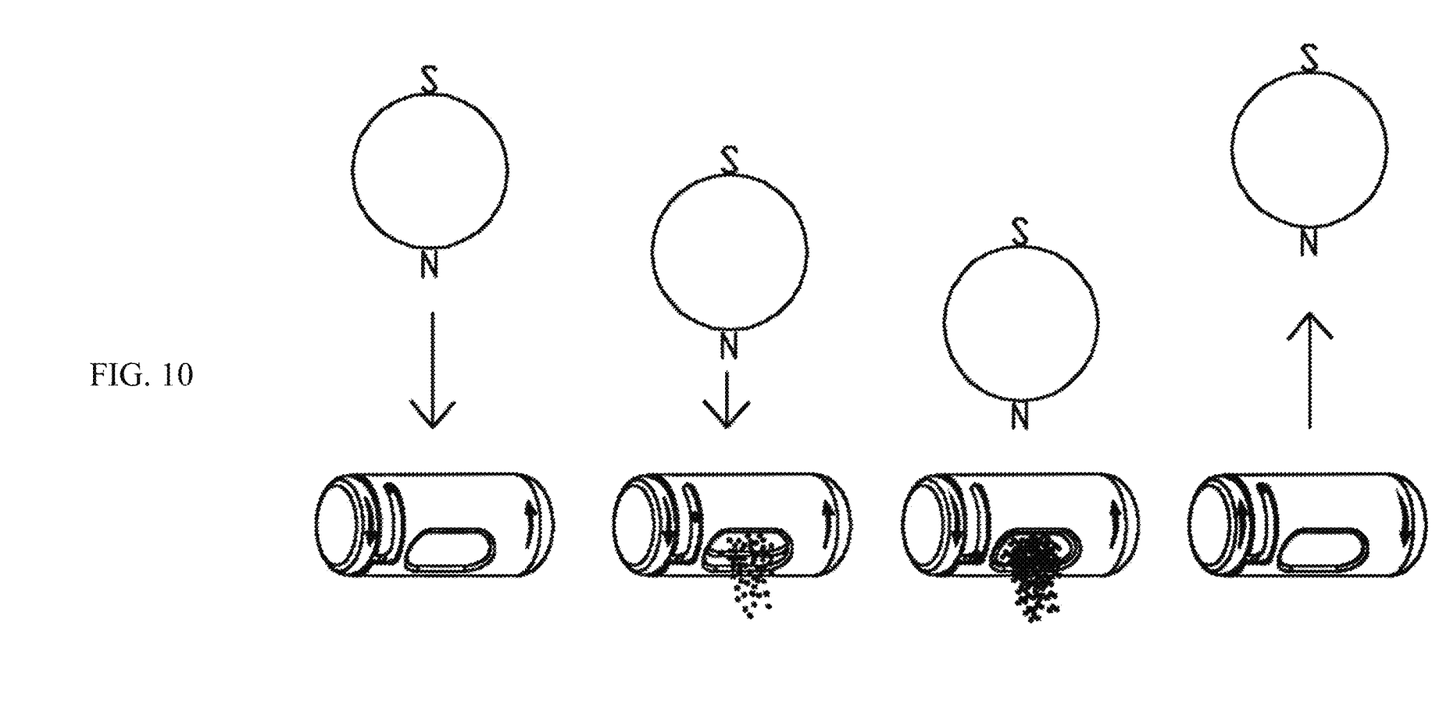
FIG. 10 shows a schematic illustration of the digestive tract medication administration system in service.

Referring to FIG. 10, a schematic illustration of digestive tract medication administration system in service 100 in service. When the external magnetic field is not applied, the administering windows of the capsule 120 are closed; when the external magnetic field is applied, magnetic force begins to act on the magnetic cylinders in the medication administration capsule 120, and as the external magnetic field approaches the medication administration capsule 120, the administering windows begin to open gradually until fully opened, reaching the maximum dosage of administration. When the external magnetic field is removed, the medication administration capsule 120 returns to the state where administering windows are misaligned and covered up.

Depending on the structure, when the medication administration capsule 120 reaches the targeted lesion, an external magnetic field applied to open the administering windows to release medicinal powders 125 in the medication administration capsule 120. Meanwhile, the digestive juice comes into contact with the administering window and the medicinal powders 125 to accelerate its release. When the medication administration capsule 120 does not reaches the targeted lesion, in accordance with the angle requirement, the administering windows are automatically closed as the external magnetic field is not applied, so that no medicinal powders 125 are released. Therefore, the purpose of administration of medications to a targeted lesion for treatment can be achieved, so as to improve therapeutic effect and save the cost of medicinal powders.

Figure 11:
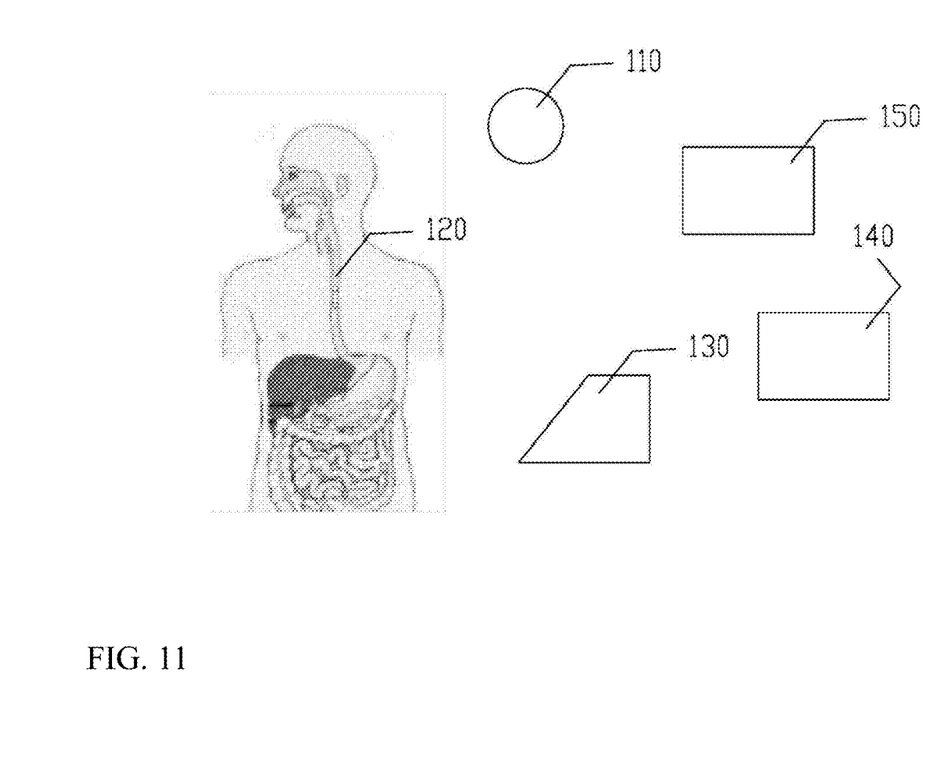
FIG. 11 shows an overall structural view of the digestive tract medication administration system.

In practical application, it is necessary to first detect the preset position of the medication administration capsule 120 in the human body, and then apply an external magnetic field to control the medication administration capsule 120 to administer medications. In order to determine the position of the medication administration capsule 120 in the digestive tract (GI tract), as shown in FIG. 11, the magnetically controlled capsule-based digestive tract medication administration system 100 disclosed herein further comprises a position detection unit 130 and a wireless communication unit 140 between which there is a communication of signals. The position detection unit 130 is configured in the medication administration capsule 120 for detecting position information of the medication administration capsule 120, and the wireless communication unit 140 is configured to receive the position information transmitted from the position detection unit 130, and send the position information to an external device 150. The external device 150 is designed with an image display from which the operator or the external control device can obtain the position information of the medication administration capsule 120 in human body to determine whether or not to apply an external magnetic field. In one embodiment of the present invention, the external device is a computer with an image display. In one embodiment of the present invention, the external control device may be a smart device such as a computer, a tablet computer, or a mobile phone that can give control commands.

The methods for detecting the position information of the medication administration capsule 120 include but not limited to the followings:

In one embodiment of the present invention, the position detection unit 130 comprises a timer and a data transmitting and receiving unit. A medication administration time length is preset in the timer, which may be an average value summarized by the medical institution, or the value obtained in previous medication administration, or the average value summarized according to the time values of multiple medication administrations. Based on a running time collected by the timer and the preset medication administration time length, whether or not the medication administration capsule 120 has reached an expected position is determined. The data transmitting and receiving unit is configured for data transmission with the wireless communication unit 140. In the preferred embodiment, the timer calculates the running time of the medication administration capsule 120 in the digestive tract, and compares the running time with the preset medication administration time length, and when the running time reaches the preset medication administration time length (that is, running time=preset medication administration time length), it is determined that the capsule 120 has reached the expected position; the data transmitting and receiving unit transmits the information that the capsule has reached the expected position to the external device 150 via the wireless communication unit 140. Then, the operator or external control device can decide whether or not to apply an external magnetic field.

In another embodiment of the present invention, the position detection unit 130 is a pH sensor. The pH sensor can select the pH ranges according to the desired regions to be detected. In an example, the pH sensor can accurately detect the pH values in ranges 2-12, 4-8, or 7.6-8. According to the existing medical experience, the human stomach is acidic while the duodenum is alkaline. Therefore, by means of the pH value detected, it can be determined whether the capsule 120 is in the stomach or the intestine. The pH in colon is around 7.8, so the pH sensor using the pH detection range of 7.6-8 can effectively detect whether the medication administration capsule 120 is in the colon.

In another embodiment of the present invention, the position detection unit 130 employs a magnetic field tracking method to detect the position of the capsule 120. The position detection unit 130 comprises a number of magnetic dipole units which are configured along the digestive tract of human body. The magnetic dipole unit may be a magnetic dipole moment having a current density of 0.1 A/cm^2 to 1 A/cm^2 and a weight of 0.5 g-5 g. The magnetic dipole units input movement positions of the medication administration capsule 120 into a preset digestive tract diagram, and the position of the medication administration capsule 120 in the digestive tract is determined according to the preset digestive tract diagram.

In still another embodiment of the present invention, the position detection unit 130 comprises an external sensing unit placed near the ileocecal valve of patient to detect whether the medication administration capsule is in the colon. Once the medication administration capsule 120 enters the colon, the unit can detect a signal and thereby determine the exact entry time. Several detection methods are available for the external sensing unit, including but not limited to: body surface magnetic field detection, radio frequency (RF) detection, or ultrasonic sensing.

In still another embodiment of the present invention, the position detection unit 130 is an enzyme sensor located outside the medication administration capsule 120. In an example, the unit is an enzyme sensor located on the outer shell 122 of the medication administration capsule 120. The enzyme sensor is used to detect whether or not enzyme exists in the regions of digestive tract, such as an enzyme sensor specifically for detecting the presence of enzyme in colon. If enzyme is detected in colon, the enzyme sensor sends a signal to the external device 150 through the wireless communication unit 140 to confirm that the medication administration capsule 120 has reached the colon.

In still another embodiment of the present invention, the position detection unit 130 comprises a number of external sensors which are configured along the digestive tract of human body. The external sensing device can be, but not limited to, a magnet, an RF unit, or an ultrasonic sensing unit. When the medication administration capsule 120 is moving in the digestive tract, one of the external sensors, closest to the capsule 120, senses the strongest signal, and thereby the position of the capsule 120 is determined.

In accordance with the methods described above, after the position detection unit 130 determines that the capsule 120 has reached the expected position, the operator or external control device applies an external magnetic field to the medication administration capsule 120, controlling the administering windows to open and close for release of medications.

In summary, in the magnetically controlled digestive tract medication administration system disclosed herein, the first magnetic cylinder 123 is embedded in the inner shell 121 and the second magnetic cylinder 124 is embedded in the outer shell 122. Even when the external magnetic field is not applied, as required by the assembly angle of the rotation limit slot 1228 and the rotation limiting pin 1218, there is an angle α between the N-S directions of the first magnetic cylinder 123 and the second magnetic cylinder 124, so that there are mutual attraction and torque between the two magnetic cylinders, making the medication administration capsule 120 always assembled. When an external magnetic field is applied, the relative rotation between the first magnetic cylinder 123 and the second magnetic cylinder 124 increases the angle between the two magnetic cylinders, and thereby increases the torque between the two magnetic cylinders. In another aspect of the invention, rotation between the magnetic cylinders 123 and 124 drives the inner shell 121 and the outer shell 122 to rotate relatively, causing the administering windows 1215 and 1225 thereon to be misaligned, and thereby making the administering windows 1215 and 1225 closed or opened depending on whether an external magnetic field is applied or not. In addition, there is mutual attraction between the first magnetic cylinder 123 and the second magnetic cylinder 124, which can firmly combine the inner shell 121 and the outer shell 122 and ensure no separation along the axial direction of the medication administration capsule 120.

Optionally, internal threads 1227 are cut at the circular opening 1226 of the outer shell 122 and external threads 1217 are cut at corresponding position of the inner shell 121. The threaded connection further ensures that the inner shell 121 and the outer shell 122 can not separate along the axial direction of the capsule 120.

Based on the design described above, the structure of the medication administration capsule is simplified, and when the size of the medication administration capsule is constant, the volume occupied by the medicinal powders can be larger, so that more medications can be released, and the capsule capacity is thereby increased. In addition, by control of external magnetic field, administration of medications to a targeted lesion can be achieved, making treatment more targeted, and improving the therapeutic effect while reducing unnecessary waste of the medicinal powders.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in particular the matters of shape, size and arrangement of parts within the principles of the present disclosure, up to and including the full extent established by the broad general meaning of the terms used in the claims.

What is claimed is:

1. A capsule for administering a medication, comprising:
   an inner shell, an outer shell, a first magnetic cylinder, a second magnetic cylinder and a drug powder, wherein:
   the inner diameter of the outer shell is larger than the outer diameter of the inner shell, and the outer shell and the inner shell are coupled;
   the first magnetic cylinder is affixed to the inner shell, wherein the outer surface of the first magnetic cylinder is affixed to the inner surface of the inner shell;
   the second magnetic cylinder is affixed to the outer shell, wherein the outer surface of the second magnetic cylinder is affixed to the inner surface of the outer shell;
   the first magnetic cylinder and the second magnetic cylinder are radially polarized, and when an external magnetic field is not applied to the capsule, the angle between lines connecting the N and S pole of the first magnetic cylinder and the second magnetic cylinder, respectively, is greater than 0° and less than 90°;
   the drug powder is in between the first magnetic cylinder and the second magnetic cylinder; and
   when an external magnetic field is applied to the capsule, at least one of the first magnetic cylinder and the second magnetic cylinder rotates along a central axis of the capsule.

2. The capsule of claim 1, wherein at least one administering window is formed in the annular wall of the outer shell, an equal number of administering windows are formed in the annular wall of the inner shell, and the administering windows in the outer shell and the inner shell are matched in pairs; wherein when no external magnetic field is applied to the capsule, the paired administering windows are misaligned and covered by the outer shell and the inner shell; and wherein when an external magnetic field is applied to the capsule, the paired administering windows align and fully open as the outer shell and the inner shell rotate under the external magnetic field.

3. The capsule of claim 1, wherein the outer shell has a circular cup-shaped structure, comprising a cup bottom, an annular wall extending from and perpendicular to the cup bottom, and an circular opening opposite to the cup bottom; and wherein a rotation limiting slot is formed in the annular wall close to the circular opening; and wherein the inner shell of the capsule has a cap-shaped structure comprising a cap top and an annular wall perpendicular to the cap top; wherein a rotation limiting pin is set near a junction of the cap top and the annular wall.

4. The capsule of claim 3, wherein the rotation limiting slot comprises an entrance part at an angle to a plane of a circular opening and a movement part parallel to the plane of the circular opening, and the entrance part is connected to the movement part.

5. The capsule of claim 4, wherein the administering window in the outer shell is next to the entrance part of the rotation limiting slot and the administering window in the inner shell is next to the rotation limiting pin.

6. The capsule of claim 2, wherein two administering windows are formed in the annular wall of the outer shell and two administering windows are formed in the annular wall of the inner shell; and the administering windows in the outer shell and the inner shell are matched in pairs; wherein when no external magnetic field is applied to the capsule, the paired administering windows are misaligned and covered by the outer shell and the inner shell; and wherein when an external magnetic field is applied to the capsule, the paired administering windows align and fully open as the outer shell and the inner shell rotate under the external magnetic field.

7. The capsule of claim 6, wherein the two administering windows in the outer shell are located at two sides of the rotation limiting slot; and the two administering windows in the inner shell are symmetrical around the central axis of the capsule, one of which is located next to the rotation limiting pin.

8. The capsule of claim 2, wherein three or more administering windows are formed in the annular wall of the inner shell, and the same number of administering windows are formed in the annular wall of the inner shell; and the administering windows in the outer shell and the inner shell are matched in pairs; wherein when no external magnetic field is applied to the capsule, the paired administering windows are misaligned and covered by the outer shell and the inner shell; and wherein when an external magnetic field is applied to the capsule, the paired administering windows align and fully open as the outer shell and the inner shell rotate under the external magnetic field.

9. The capsule of claim 3, wherein internal threads are provided at the circular opening of the outer shell, and external threads are cut at the junction of the cap top and the annular wall of the inner shell, and the external threads fit the internal threads.

10. A digestive tract medication administration system, comprising:
    an external magnet and a medication administering capsule, wherein the external magnet locates is located outside a human body, and the medication administering capsule is orally administered to the digestive tract of the human body;
    wherein the medication administration capsule comprises an inner shell, an outer shell, a first magnetic cylinder, a second magnetic cylinder and a drug powder, wherein:
    the inner diameter of the outer shell is larger than the outer diameter of the inner shell, and the outer shell and the inner shell are coupled;
    the first magnetic cylinder is affixed to the inner shell, wherein the outer surface of the first magnetic cylinder is affixed to the inner surface of the inner shell;

the second magnetic cylinder is affixed to the outer shell, wherein the outer surface of the second magnetic cylinder is affixed to the inner surface of the outer shell;

the first magnetic cylinder and the second magnetic cylinder are radially polarized, and when an external magnetic field is not applied to the capsule, the angle between lines connecting the N and S pole of the first magnetic cylinder and the second magnetic cylinder, respectively, is greater than 0° and less than 90°;

the drug powder is in between the first magnetic cylinder and the second magnetic cylinder; and when an external magnetic field is applied to the capsule, at least one of the first magnetic cylinder and the second magnetic cylinder rotates along a central axis of the capsule.

11. The digestive tract medication administration system of claim 10, further comprising a position detection unit and a wireless communication unit, wherein the wireless communication unit communicates with the position detection unit; the position detection unit is in the medication administration capsule for detecting position information of the medication administration capsule; and the wireless communication unit receives the position information transmitted from the position detection unit, and sends the position information to an external device.

12. The digestive tract medication administration system of claim 11, wherein the position detection unit comprises a timer and a data transmitting and receiving unit; a medication administration time is preset in the timer, whether the medication administration capsule has reached an expected position or not is determined based on the preset medication administration time; and the data transmitting and receiving unit sends the position information to the wireless communication unit when the medication administration capsule reaches the expected position.

13. The digestive tract medication administration system of claim 11, wherein the position detection unit is a pH sensor which determines the position of the medication administration capsule according to the pH value detected.

14. The digestive tract medication administration system of claim 11, wherein the position detection unit is an external sensing unit placed near the ileocecal valve of patient to detect whether the medication administration capsule is in the colon.

15. The digestive tract medication administration system of claim 11, wherein the position detection unit is an enzyme sensor located outside the medication administration capsule for detecting whether or not enzyme exists in the regions of digestive tract.

16. The digestive tract medication administration system of claim 11, wherein the position detection unit comprises a plurality of external sensors which are configured along the digestive tract of human body; one of the external sensors which is closest to the capsule, senses the strongest signal when the capsule is moving in the digestive tract, and the position of the capsule is determined based on the strongest signal.

17. The digestive tract medication administration system of claim 11, wherein the position detection unit comprises a plurality of magnetic dipole units which are configured along the digestive tract of human body; the magnetic dipole units input movement positions of the medication administration capsule into a preset digestive tract diagram, and the position of the capsule in the digestive tract is determined according to the digestive tract diagram.

* * * * *